United States Patent [19]
Jampani et al.

[11] Patent Number: 6,080,416
[45] Date of Patent: *Jun. 27, 2000

[54] LOW TACK LOTION, GELS AND CREAMS

[75] Inventors: Hanuman B. Jampani, Grapevine; Anthony W. Newman, Fortworth, both of Tex.

[73] Assignee: Ethicon, Inc., Somerville, N.J.

[ * ] Notice: This patent is subject to a terminal disclaimer.

[21] Appl. No.: 09/376,142

[22] Filed: Aug. 17, 1999

Related U.S. Application Data

[62] Division of application No. 09/009,489, Jan. 20, 1998, Pat. No. 5,972,358.

[51] Int. Cl.$^7$ .............................. A61K 7/00; A61K 7/06; A61K 31/74; A61K 9/14
[52] U.S. Cl. ................... 424/401; 424/70.12; 424/78.03; 424/484; 514/844; 514/937; 514/943; 514/944
[58] Field of Search ...................................... 424/401, 484, 424/70.12, 78.03; 514/844, 937, 943, 944

[56] References Cited

U.S. PATENT DOCUMENTS

| | | |
|---|---|---|
| 2,798,053 | 7/1957 | Brown . |
| 3,133,865 | 5/1964 | Richardson et al. . |
| 3,886,277 | 5/1975 | Randebrock et al. . |
| 4,134,412 | 1/1979 | Gross et al. . |
| 4,257,907 | 3/1981 | Langguth et al. . |
| 4,268,424 | 5/1981 | Hall et al. . |
| 4,303,543 | 12/1981 | Mansy . |
| 4,326,997 | 4/1982 | Willis et al. . |
| 4,402,881 | 9/1983 | Gross et al. . |
| 4,426,310 | 1/1984 | Verunica . |
| 4,464,293 | 8/1984 | Dobrin . |
| 4,474,807 | 10/1984 | Gerhardt et al. . |
| 4,690,821 | 9/1987 | Smith et al. . |
| 4,804,750 | 2/1989 | Nishimura et al. . |
| 4,816,451 | 3/1989 | Schriewer et al. . |
| 4,849,455 | 7/1989 | Eggers et al. . |
| 4,923,862 | 5/1990 | Hirota . |
| 4,956,170 | 9/1990 | Lee . |
| 4,957,908 | 9/1990 | Nelson . |
| 4,966,754 | 10/1990 | Purohit et al. . |
| 5,004,598 | 4/1991 | Lochead et al. . |
| 5,053,407 | 10/1991 | Hayakawa et al. . |
| 5,098,717 | 3/1992 | Blackman . |
| 5,109,019 | 4/1992 | Lehmann et al. . |
| 5,164,107 | 11/1992 | Khan et al. . |
| 5,180,061 | 1/1993 | Khan et al. . |
| 5,180,749 | 1/1993 | Cusack et al. . |
| 5,288,486 | 2/1994 | White . |
| 5,298,242 | 3/1994 | Vanlerberghe et al. . |
| 5,308,890 | 5/1994 | Snyder . |
| 5,326,492 | 7/1994 | Hodam, Jr. . |
| 5,335,373 | 8/1994 | Dangman et al. . |
| 5,336,305 | 8/1994 | Staats . |
| 5,401,741 | 3/1995 | Saro et al. . |
| 5,403,587 | 4/1995 | McCue et al. . |
| 5,403,864 | 4/1995 | Bruch et al. . |
| 5,416,109 | 5/1995 | Donofrio et al. . |
| 5,420,104 | 5/1995 | Holzner et al. . |
| 5,512,199 | 4/1996 | Khan et al. . |
| 5,540,853 | 7/1996 | Trinh et al. . |
| 5,607,681 | 3/1997 | Galley et al. . |
| 5,626,837 | 5/1997 | Shimada et al. . |
| 5,661,170 | 8/1997 | Chodosh . |
| 5,665,742 | 9/1997 | Mori et al. . |

FOREIGN PATENT DOCUMENTS

| | | |
|---|---|---|
| 600269 | 5/1987 | Australia . |
| 2 326 167 | 12/1998 | United Kingdom . |
| WO 94/27436 | 8/1994 | WIPO . |

OTHER PUBLICATIONS

Chemical Abstracts, Jones, M.N. et al., "The Use of Phospholipid Liposomes for Targeting to Oral and Skin–Associated Bacteria", vol. 122, No. 8, pp. 381–389, 1994.

Lee W. Bush, Leslee M. Benson, and John H. White, Pig Skin Test Subtrate for Evaluating Topical Antimicrobial Activity, Sep. 1986, Journal of Clinical Microbiology.

*Primary Examiner*—Shelley A. Dodson
*Assistant Examiner*—Marina Lamm

[57] ABSTRACT

The present invention relates to a mixture of a silicone wax, a silicone fluid and two long chain lactate molecules which is effective in reducing the tacky feel of compositions. The present invention is suitable for use in creams, gels, lotions and salves that are applied to the skin.

6 Claims, No Drawings

LOW TACK LOTION, GELS AND CREAMS

RELATED APPLICATIONS

This is a Divsional of prior application Ser. No. 09/009,489, filed Jan. 20, 1998, U.S. Pat. No. 5,972,358.

This application is related to my U.S. patent applications, Ser. No. 09/009,596, entitled ANTI-MICROBIAL COMPOSITION; and Ser. No. 09/009,491, entitled ALCOHOL BASED ANTI-MICROBIAL COMPOSITIONS WITH COSMETIC APPEARANCE, all concurrently filed herewith and which are assigned to assignee of the present invention and incorporated by reference as if fully set forth herein.

The present invention relates to lotions, gels and creams which are less sticky, more particularly to lotions and creams that contain lactate and silicone waxes.

BACKGROUND OF THE INVENTION

Topical skin care formulations or products are being developed to provide moisturization without any greasiness or tackiness to maintain the skin integrity. In recent years alcohol based formulations are gaining importance in not only professional sector but also within the consumer sector, as consumer seek to find compositions with antibacterial and moisturization properties. It is well known that alcohols, such as ethyl alcohol, iso-propyl alcohol and n-propyl alcohol are dehydrating in nature when applied on skin. To reduce the dehydrating properties of alcohols certain moisturizers, emollients agents are being added. Unfortunately such product development efforts, typically many components are considered to formulate which could cause or contribute to undesirable features in the end product like tackiness, greasiness and unpleasant feel. In order to overcome these undesired attributes some detackifying compounds are employed in the formulation.

One such class of compounds disclosed in the prior art are silicones. Similarly, long chain lactate molecules are also in use as tack reducing components in a multi component matrix systems such as emulsions, cleansing lotions, creams, aqueous and non-aqueous based gels and other topical formulations that are used by hospital professionals and consumers.

For example, U.S. Pat. No. 4,423,041 discloses a detackifying composition for use in emulsion-type personal care compositions comprising a mixture of a silicone fluid and silicone wax in a ratio of 9:1 to 1:3. Despite this and other disclosures there is an ongoing need for a effective detackifying system for creams and lotions.

SUMMARY OF THE INVENTION

The particular invention is a composition comprising polymeric silicones in combination with lactate molecules. The polymeric silicones employed in the present invention are stearoxy trimethyl silane and cyclomethicone. The lactates used in the present invention are cetyl lactate and long chain alkyl lactate. The weight ranges between the stearoxy trimethyl silane and cyclomethicone is from about 1:75 to about 1:40; and the weight ratio between the cetyl lactate and the $C_{12}$–$C_{15}$, alkyl lactates is from about 1:2 to about 1:5. When the combination of two silicones are used in presence of moisturizers such as glycerin, water, lipids, waxes, essential oils, acrylic polymers, a reduction of tack in the end was noted. A method for reducing the tackiness of creams, gels lotions and the like are also provided.

DETAILED DESCRIPTION OF THE INVENTION

The present invention contains from about 0.01 to about 0.50 of stearoxy trimethyl silane, preferably from about 0.02 to about 0.10 and most preferably about 0.025 weight percent. The level of cyclomethicone is from about 0.5 to about 2.5, preferably from about 0.75 to about 2.0 and most preferably from about 1.0 to about 1.5 weight percent. The level of cetyl lactate is from about 0.25 to about 2.5 weight percent, preferably from about 0.4 to about 2.0 and most preferably from about 0.5 to about 1.5 weight percent. The level of alkyl ($C_{12}$–$C_{15}$) lactates employed in the present invention ranges from about 0.25 to about 2.5 weight percent, preferably from about 0.3 to about 2.0 and most preferably from about 0.4 to about 1.5 weight percent. The weight ratio of the stearoxy trimethyl silane to the cyclomethicone is preferably from 1:50 to about 1:60. The weight ratio of the cetyl lactate to the alkyl lactate is preferably from about 1:2 to about 1:4.

This present invention has wide applications in developing tack reducing compositions or product formulations which are dermatologically acceptable. These detackifying combinations allow the formulation of products which are topically applicable to provide good feel with protection from environment. Particularly these tack reducing compositions are important in complex formulations like water/oil and oil/water emulsions, mineral oil or petrolatum based creams, alcoholic gels, high glycerin containing topical skin care products.

The tack reducing composition of the present invention are in addition to other ingredients typically found in hand creams, gels and lotions. Such materials include but are not limited to thickeners, antimicrobial agents, solvents, fragrances, emollients, pH adjusters, viscosity modifiers, transdermal enhancers, surfactants, dyes, colors and the like.

In a particularly preferred embodiment the tack reducing compounds of the present invention are used in a substantially waterless antiseptic gel wherein alcohol such as ethyl alcohol, iso-propyl and n-propyl alcohols are used.

The alcohol level in these waterless antiseptic/antibacterial gels are typically from about 20 to about 55 weight percent. In these systems a preferred embodiment of the invention employs stearoxy trimethyl silane at about 0.025 weight percent; cyclomethicone at about 1.25 weight percent; cetyl lactate at about 0.5 weight percent; and $C_{12}$–$C_{15}$, alkyl lactates at about 1.5 weight percent.

Stearoxy trimethyl silane is not completely soluble in high content alcohol systems or alcoholic mixtures, and in such instances the Silsoft® PEDM (phenylethyl dimethicone) an organosilicone liquid is a good media to disperse the softened wax, and make it compatible with the system. In the absence of such a solvent, the wax may appear on hands as flakes due to recrystallization of the wax on the hands or due to rapid evaporation of alcohol.

A preferred cyclomethicone is commercially available as Dow Corning® 245 fluid. Cyclomethicone is a silicone oil which consists of decamethyl cyclopenta siloxane. Also commercially available and useful in the present invention is Dow Corning® 580 wax, a mixture of stearoxy trimethyl silane and stearyl alcohol, a semicrystalline silicone wax. The ratio between these two silicones along with the lactates is critical in presence of synergistic alcohols such as ethyl alcohol, isopropyl alcohol and n- propyl alcohol and other ingredients like glycerin, water, acrylic acid based carbomers as well as other thickeners, volatile oils, terpenes and other fragrances, and lipids. The combination of alkyl lactates such as cetyl lactate (CERAPHYL®-28) and $C_{12}$-$C_{15}$ alkyl lactate (CERAPHYL®-41) in presence of silicone fluid and silicone wax has shown an improved tack reduction. When the ratio of the composition are not employed in the desired ratios results in undesirable flaking and balling on the hands after application of the product. Balling is the process of forming small balls believed to be formed from the thickening agents and other ingredients of the formulation. Balling is believed to be the result of a lack of sufficient moisture in the formulation, causing the formulation to become unstable and the ingredients to be deposited in small balls in the hand.

Conversely, when the lactate molecules are employed in formulations containing above said tack inducing agents, tack was noted with the end products. It has been surprisingly discovered that the addition of lactates to the mixture of silicones in the specified ratios reduced the level of tackiness in the product. The addition of the lactates in the prescribed levels reduced the evaporation rate of the product, thereby also moisturizing the hands and imparting a smooth and supple feeling. This supple feeling imparted by the product is important to consumers, doctors and nurses, who will be using the product.

Without wishing to be bound by any theory the present invention is believed to be due to formation of a mixture that evaporates rapidly leaving a protective layer of silicones and lactate molecules as an effective barrier.

This barrier is believe to prevent rapid loss of skin moisture. This feature of any product has an added advantage in particular with hydroalcoholic gels which have inherent dehydrating properties. The tack reducing compositions will also allow the consumer of the product containing the invention to put on latex gloves much faster than otherwise and provides extra protection for hands in terms of maintaining skin temperature and antimicrobial protection obtained by alcohol or antimicrobial compositions.

The following compositions were used in the present invention:

CERAPHYL-28 is primarily cetyl lactate, a waxy solid available from ISP Van Dyk Inc.
CERAPHYL-41 is a mixture of $C_{12}$–$C_{15}$ alcohol lactates, available from ISP Van Dyk Inc.
ULTREZ 10 a carbomer polymer useful as a thickener available from BF Goodrich.

The following examples are presented for the purpose of illustrating the present invention and is not intended to limit the invention to those examples presented below. Unless otherwise noted all weights are understood to be weight percent. In the following examples the short chain alcohols are listed by volume.

EXAMPLES

Several hydroalcoholic formulations were prepared using this combination as shown in the below examples (Table 1). It is also applicable to most of the topical formulations which would need tack free attribute in compositions such described in this invention.

Formulation 1 ethyl alcohol 60.5; ULTREZ 10 0.45; glycerin 0.5; cylomethicone (245) 1.25; Dow Corning 580 wax 0.025; SILSOFT PEDM 0.2; CERAPHYL-41 1.0; CERAPHYL-28 0.5; AMP -95; fragrance 0.12 and deionized water.

Formulation 2 same as Formulation 1 above plus Australian tree oil 2.0 and Phospholipid CDM 0.05.

Formulation 3 same as Formualtion 2 except that the ethyl alcohol was removed and replaced with ethyl alchol 40.5; iso-propyl alcohol 15; and n-propyl alcohol 5.

Formulation 4 same as Formulation 1 except that the ethyl alcohol was removed and replaced with ethyl alchol 40.5; iso-propyl alcohol 15; and n-propyl alcohol 5.

Formulation 1 was used as a control. This formulation was not tacky but did not contain other ingredients commonly used in creams, lotions and gels for moisturizing and providing soft supple hands.

Formulations 2, 3 and 4 were found to be non-tacky when used with alcohol mixtures, essential oils such as Australian tea tree oil, and phospholipid. This example demonstrates that the tack reducing composition is effective in the presence of emollients, moisturizers and high-boiling solvents, such as iso-propyl alcohol and n-propyl alcohol, and when used at various concentrations.

We claim:

1. A hydroalcohol detackifying mixture comprising from about 0.01 to about 0.5 weight percent stearoxy trimethyl silane; from about 0.5 to about 2.5 weight percent cyclomethicone; from about 0.25 to about 2.5 weight percent cetyl lactate; and from about 0.25 to about 2.5 weight percent $C_1$–$C_{15}$ alkyl lactates; wherein the weight ratio of stearoxy trimethyl silane to cyclomethicone is about 1:75 to about 1:40 and the weight ratio of cetyl lactate to $C_{12}$–$C_{15}$ alkyl lactates is from about 1:1 to about 1:5; about from about of from about 40 to about 80 percent by volume selected from the group consisting of ethyl alcohol, iso-propyl alcohol and n-propyl alcohol; and water.

2. The mixture of claim 1 wherein the weight ratio of stearoxy trimethyl silane to cyclomethicone is from about 1:50 to about 1:60.

3. The mixture of claim 1 wherein the weight ratio of cetyl lactate to $C_{12}$–$C_{15}$ alkyl lactates is from about 1:2 to about 1:4.

4. The mixture of claim 1 wherein the concentration of stearoxy trimethyl silane is about 0.025 weight percent, cyclomethicone is about 1.25 weight percent, cetyl lactate is about 0.5 weight percent and $C_{12}$–$C_{15}$ alkyl lactates is about 1.0 weight percent.

5. The mixture of claim 1 wherein the alcohol is ethyl alcohol.

6. The mixture of claim 1 wherein the mixture contains about 45 weight percent ethyl alcohol, about 10 weight percent iso-propyl alcohol and about 5 weight percent n-propyl alcohol.

* * * * *

UNITED STATES PATENT AND TRADEMARK OFFICE
CERTIFICATE OF CORRECTION

PATENT NO. : 6,080,416
DATED : June 27, 2000
INVENTOR(S) : Jampani & Newman

It is certified that error appears in the above-indentified patent and that said Letters Patent is hereby corrected as shown below:

In claim 1, line 6, kindly delete "$C_1$" and insert in its place --$C_{12}$--

Signed and Sealed this

Tenth Day of April, 2001

Attest:

NICHOLAS P. GODICI

Attesting Officer     Acting Director of the United States Patent and Trademark Office